United States Patent [19]

Soika

[11] 4,205,819

[45] Jun. 3, 1980

[54] FLOW CLAMP DEVICE

[76] Inventor: Emil Soika, 2312 E. Grand Ave., Lindenhurst, Ill. 60046

[21] Appl. No.: 916,602

[22] Filed: Jun. 19, 1978

[51] Int. Cl.² ............................................. F16K 7/06
[52] U.S. Cl. ......................................... 251/9; 251/340
[58] Field of Search ...................... 251/4, 8, 9, 340, 6, 251/212

[56] References Cited

U.S. PATENT DOCUMENTS

| 492,580 | 2/1893 | Hadley | 251/9 X |
|---|---|---|---|
| 1,865,012 | 6/1932 | Jackson | 251/9 X |
| 2,825,333 | 3/1958 | Broman | 128/214 |
| 3,497,175 | 2/1970 | Koland | 251/9 |
| 3,612,474 | 10/1971 | Strohl | 251/9 |

FOREIGN PATENT DOCUMENTS 716500 1/1942 Fed. Rep. of Germany ........... 251/340

Primary Examiner—Martin P. Schwadron
Assistant Examiner—Richard Gerard

Attorney, Agent, or Firm—Merriam, Marshall & Bicknell

[57] ABSTRACT

An adjustable clamp for controlling the flow of fluid through a flexible tubing having deformable walls has an elongated, externally threaded body having an axial bore through which the tubing passes. One end of the body contains one or more longitudinally slots communicating with the bore, in which slot is located an elongated arm or wing hinged at one of its ends to the body, the other end of the arm being free to move radially within the slot. The radial height of the arm tapers, being a maximum at its free end and a minimum at its hinged end. A threaded nut engaging the thread on the body is provided with a bearing surface which contacts the tapered surface of the arm. As the nut is turned in a direction to move it towards the slotted end of the body, the arm is progressively forced into the slot, deforming the enclosed tubing to an increasing degree, thereby permitting control of the flow of fluid through the tubing.

5 Claims, 5 Drawing Figures

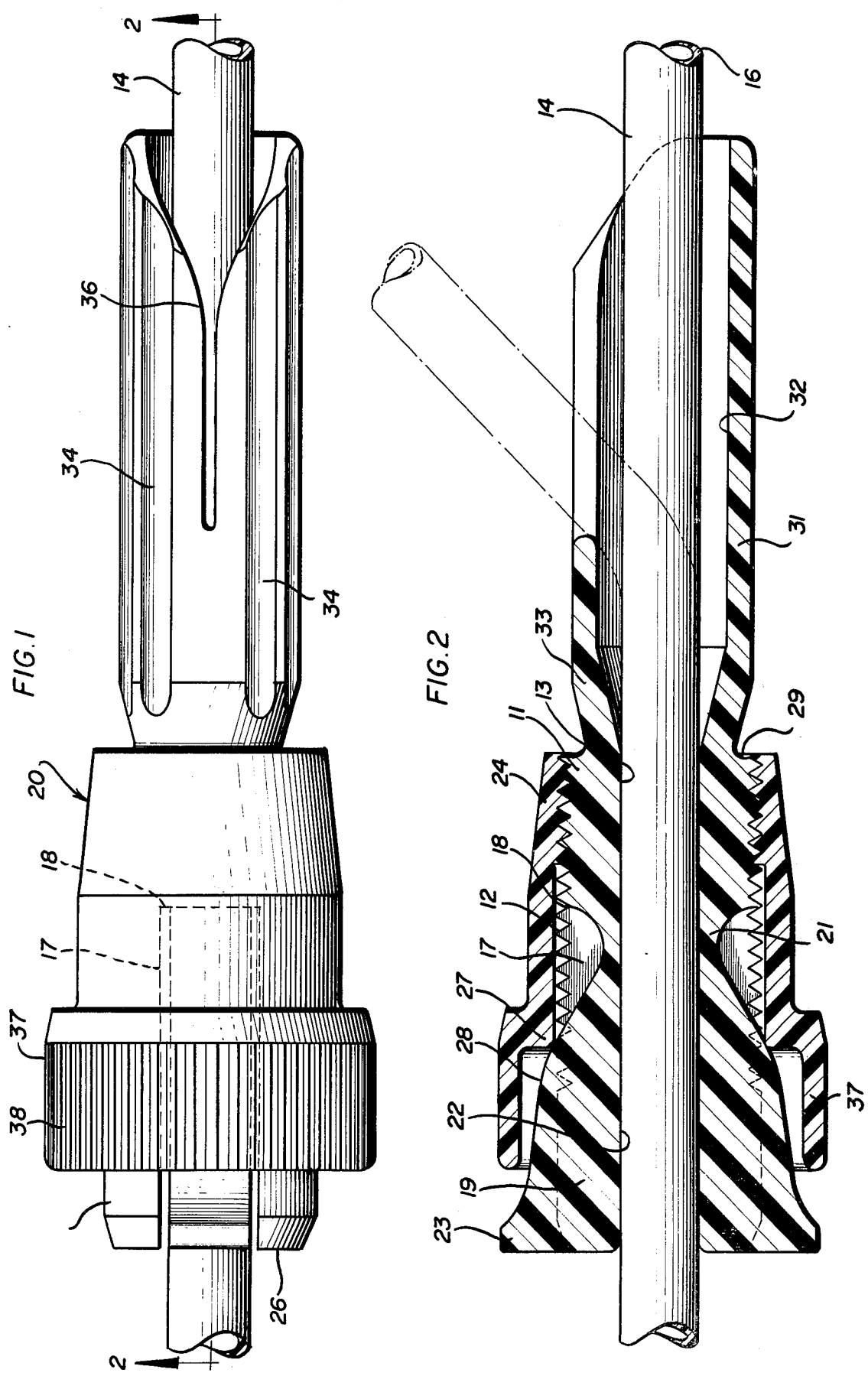

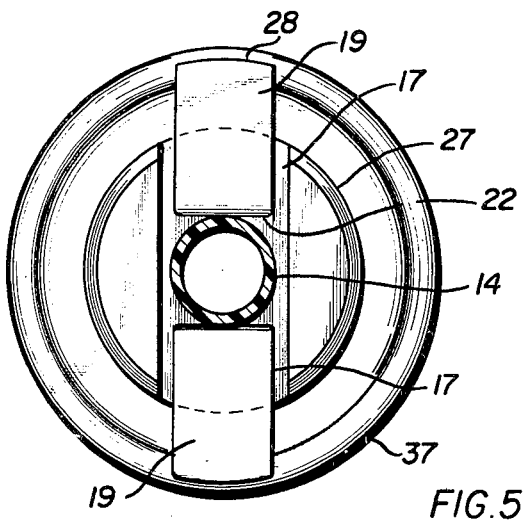
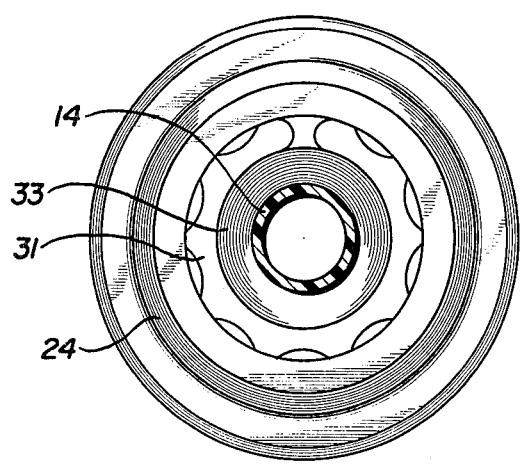
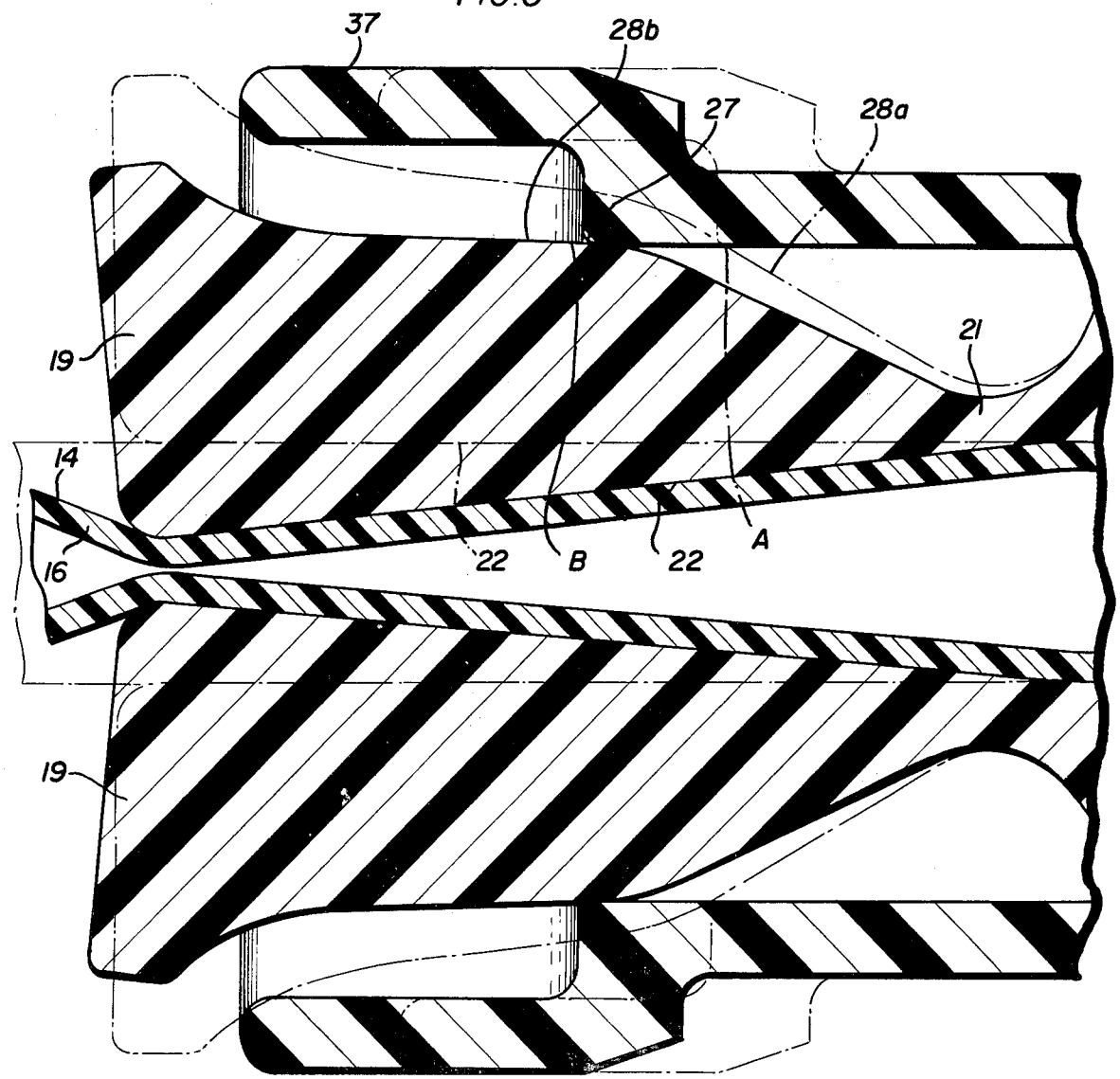

FLOW CLAMP DEVICE

This invention relates to an improved adjustable clamp for controlling the flow of fluid through a flexible tubing having deformable walls.

BACKGROUND OF THE INVENTION

The intravenous administration of fluids into the human body is a routine medical procedure, typically one in which a liquid solution containing a nutrient or a drug is allowed to flow under gravity from a container through a flexible, small diameter tubing into the vein of a patient. Since in many cases it is desired that the flow be maintained at a precise low rate over a long period of time, some means for controlling the flow rate must be provided, such means typically being a clamp which deforms the walls of the tubing sufficiently to control the flow rate of the fluid passing therethrough.

A number of different clamps which function in this manner have been used or proposed, ranging from a simple spring-biased clamp capable only of on-off control, to more complex arrangements providing a finer degree of control, as shown in U.S. Pat. Nos. 1,865,012, 2,825,333, 2,954,028, 3,167,085, 3,497,175, 3,612,474 and 3,685,786.

In addition to providing precise control of fluid passing through the tubing with which it is used, particularly at low rates of flow which may be on the order of a few drops per minute, a clamp intended for this purpose desirably possesses a number of other features. The force exerted by the clamping member on the flexible tubing should be applied over a relatively large area of the tubing, so as to avoid creating a permanent set or deformation in the tubing. This is important in order to insure that the tubing, after being compressed or deformed by the clamp for a substantial period of time, will tend to resume its original shape when the clamp is loosened. Since the pressure of the flowing fluid is generally very small, the natural resiliency of the tubing must be relied on to ensure that the tube will expand to permit a greater flow as the clamping force exerted by the clamp is decreased. If the clamping force is concentrated over a small portion of the tube, there exists the possibility that the tube will be permanently deformed in this area and will lose the resiliency necessary to permit increased flow rates when the clamping force is removed.

Another desirable attribute in an adjustable tubing clamp is a dual mode of operation. In the first mode, actuation of a control member, typically a rotatable wheel or nut, rapidly closes the bore of the flexible tube until the point of flow regulation is reached, after which a given movement of the control element provides a much smaller degree of constriction in the flexible tubing, thus permitting extremely sensitive adjustment for precise regulation.

It is also desirable that a clamp of this type be capable of one-handed operation, leaving the other hand of the operator free for other functions, such as adjusting the position of a hypodermic needle through which the liquid is injected into a patient's vein. Finally, it is desirable that the clamp be inexpensive, in order to permit disposal after a single use, in keeping with preferred medical procedures.

BRIEF DESCRIPTION OF THE INVENTION

The requirements described above are met by the clamp of the invention, which comprises an elongated, externally threaded body having an axial bore of a size to admit a flexible tubing. One end of the body contains one or more longitudinal slots communicating with the bore, in which slot is located an elongated arm or wing hinged at one of its ends to the body, the other end of the arm being free to move radially within the slot. The radial height of the arm tapers, being a maximum at its free end and a minimum at its hinged end. With the lower surface of the arm in alignment with the wall of the bore in the body, the tapered upper surface of the arm extends at least in part beyond the outer surface of the body. A threaded nut engaging the thread on the body is provided with a bearing surface which contacts the tapered surface of the arm. As the nut is turned in a direction to move it towards the slotted end of the body, the arm is progressively forced into the slot, deforming the enclosed tubing to an increasing degree, thereby permitting control of the flow of fluid through the tubing. The angle of taper on the outer surface of the arm is preferably nonuniform, such that a greater movement of the arm is achieved during the initial operation of the nut than in a later stage of operation. In a preferred embodiment, the end of the body opposite its slotted end is provided with a slotted tubular axial extension through which the flexible tubing passes, affording a convenient hand-hold for one-handed operation of the clamp, as sell as a quick shut-off capability.

DESCRIPTION OF THE DRAWINGS

The invention will be better understood from the following detailed description thereof, taken in conjunction with the accompanying drawings, in which:

FIG. 1 is a top view of a preferred embodiment of the invention, in place on a section of flexible tubing;

FIG. 2 is a sectional view along the line 2—2 of the embodiment of FIG. 1;

FIG. 3 is an end view from the left side of the embodiment of FIG. 1;

FIG. 4 is an end view from the right side of the embodiment of FIG. 1; and

FIG. 5 is an enlarged detail of the left end of the embodiment of FIG. 1 illustrating the operation of the clamp.

DETAILED DESCRIPTION

As shown in the drawings, a clamp 10 in accordance with the invention comprises in a preferred embodiment an elongated generally cylindrical body 11 provided with an external helical thread 12 extending along a portion of its length. Body 11 is provided with an axial bore 13 which is preferably, but not necessarily, cylindrical, of a size to admit a flexible tube 14 having a deformable wall 16 and carrying a fluid whose rate is to be regulated.

Body 11 is provided at one end with one or more longitudinal slots 17 which extend from the end of the body 11 to an intermediate point 18 and which communicate with bore 13. In each slot, there is situated an elongated arm 19 having one end hinged to body 11 by appropriate means, such as the thin hinge section 21 shown in FIG. 2. The inner surface 22 of each arm is approximately collinear with wall 16 of bore 13. The radial height of each arm 19 tapers, varying from a maximum at the free end 23 of the arm to a minimum in the vicinity of hinge 21. The inner surface 22 of each arm 19 is preferably planar, although other configurations can also be used.

In the preferred embodiment shown in the drawings, two slots 17 are used, although different arrangements, using 1 or 3 or more slots can also be employed. In the preferred embodiment, the slots are diametrically opposed, giving the effect of a single slot extending from one side of body 11 to the other.

Mounted on body 11 is a nut 24 which is provided with an internal thread matching thread 12 on body 11. The internal thread in nut 24 can extend throughout its length or alternatively over only a portion thereof, as shown in FIG. 2, with the remainder of the bore of the nut being unthreaded and of a diameter to clear thread 12 on body 11. At the end of nut 24 facing the slotted end 26 of body 11 there is provided an annular shoulder 27 providing a bearing surface which contacts the tapered outer surface 28 of each of arms 19. As shown in FIG. 3, the cross-sectional contour of surface 28 is preferably circular, to match that of shoulder 27.

Attached to body 11 at its end 29 opposite the slotted end 26 thereof, is a tubular extension 31 coaxial with bore 13. The bore 32 of tubular extension 31 is preferably larger than the bore 13 in body 11, with a tapering transition section 33 connecting bores 32 and 13 through which tubing 14 can be inserted into the clamp. The outer surface of tubular extension 31 is preferably provided with appropriate means, such as elongated grooves 34, for providing a firm hand-hold to facilitate one-hand operation of the clamp.

Tubular extension 31 is provided in its wall with an inwardly tapering slot 36 extending from the open end of the extension, into which tubing 2 can be forcibly inserted, as shown in phantom in FIG. 2. The opposte edges of slot 36 pinch the flexible walls of tubing 14 together, thereby shutting off the flow of fluid in the tubing. In this manner, the flow in tubing 14 can be quickly stopped and started as desired, without affecting the adjustment of clamp 10.

In order to aid one-hand operation of the clamp of the invention, it is preferred to provide an annular collar 37 attached to nut 24 in the vicinity of bearing surface 27, the collar having an enlarged diameter provided on its outer surface with suitable knurling 38 to facilitate rotation of the nut.

The operation of clamp 10 is illustrated in the enlarged detail shown in FIG. 5, in which there is shown in solid outline the position assumed by arms 19 while regulating a relatively low flow rate, and in phantom the position of the arms at the start of the control sequence. before the clamp creates any restriction in the tubing. Initially, shoulder 28 contacts the outer tapered surface 28 of each arm 19 at a point A in a section 28a of the surface which is relatively sharply inclined, e.g., at a taper angle of about 30°, relative to the inner surface 22 of the arm. Suitable rotation of nut 24 causes the contact point between shoulder 27 and arms 19 to move to the left in FIG. 5, causing arms 19 to be forced into contact with flexible wall 16 of tubing 14 within the clamp, thereby pinching the tubing and reducing the flow rate therethrough. Ultimately, shoulder 27 reaches point B in FIG. 5, at which point shoulder 27 is now in contact with a second section 28b of surface 28 which has an angle of taper (e.g., 8°) less than that in the vicinity of point A. It will be seen that because of the reduced taper of section 28b in the vicinity of point B, a given axial movement of nut 24, such as that achieved by one revolution thereof, will produce less angular movement in arm 19 about hinge 21 than that produced by the same movement when shoulder 27 contacts arm 19 at point A. Accordingly, a much finer degree of control in flow rate is possible in the vicinity of point B.

In order to permit the tubing to bulge in a transverse direction as it is clamped by opposed arms 19, it is desirable to make the width of slot 17 in which arms 19 move somewhat larger than the diameter of the flexible tubing, as shown in FIG. 3. Similarly, in order to insure that the tubing will be clamped substantially across its entire cross-section, it is preferred that the width of arms 19 be at least equal to the diameter of tubing 14.

The clamp of the invention is suitably made of a plastic material such as polypropylene, permitting its production by conventional molding techniques, thereby insuring a low cost.

While the clamp has been described as applied to medical use, it is not limited thereto. As those skilled in the art will appreciate, it can be used in any application involving the control of a fluid passing through a flexible tubing.

The foregoing detailed description has been given for clearness of understanding only, and no unnecessary limitations should be understood therefrom as modifications will be obvious to those skilled in the art.

What is claimed is:

1. An adjustable clamp device for regulating the flow of fluid through a flexible tubing having deformable walls comprising:

an elongated generally cylindrical body having a first end and a second end and an axial bore adapted to receive said tubing, said body having an external helical thread extending over at least a portion of its length;

said body being provided with at least one longitudinal slot parallel to and communicating with said bore and extending from said first end of said body to an intermediate point thereof;

an elongated arm positioned within said slot, one end of said arm being hinged to said body at said intermediate point, the other end being free to move radially within said slot, said arm having a thickness substantially equal to the diameter of said bore;

the radial height of said arm tapering from a minimum value at its hinged end to a maximum value at its free end;

said arm having an inner surface which can be substantially aligned with the wall of said bore and a tapering outer surface which projects at least in part beyond the outer surface of said body when said inner surface is substantially aligned with the wall of said bore;

a nut mounted on said body, said nut having an internal helical thread which engages the thread on said body, said nut being provided with a bearing surface adapted to contact the tapered outer surface of said arm;

whereby the lower surface of said arm tends to constrict said bore to an increasing extent as said nut is rotated in a direction which moves said bearing surface toward said first, slotted end of said body.

2. A clamp in accordance with claim 1 wherein said body is provided with a pair of said slots in each of which one of said arms is located, said slots being diametrically opposed in said body.

3. A clamp in accordance with claim 2 in which the height of each of said arms is non-uniformly tapered, the angle of taper adjacent the hinged end of said arm being greater than the angle of taper adjacent the free end thereof.

4. A clamp in accordance with claim 3 in which said body is provided with a coaxial tubular extension connected to its said second end, said extension having a bore at least as large as the bore of said body, the wall of said extension having an inwardly tapering slot extending from the free end of said extension toward said body, said slot being adapted to accept and compress the wall of said tubing sufficiently to block the flow of fluid therethrough.

5. A clamp in accordance with claim 4 in which said nut is provided with an annular coaxial collar facing said first end of said body, said collar having a diameter sufficiently large to avoid contact with said body or said arms, the outer surface of said collar being suitably roughened to assist manual rotation of said collar and said nut.

* * * * *